(12) United States Patent
Bair, III et al.

(10) Patent No.: US 7,152,455 B2
(45) Date of Patent: Dec. 26, 2006

(54) RAPID GAS RECOVERY IN AN INCUBATOR SYSTEM

(75) Inventors: Richard H. Bair, III, Asheville, NC (US); Byran M. Elwood, Candler, NC (US)

(73) Assignee: Thermo Fisher Scientific Inc., Waltham, MA (US)

( * ) Notice: Subject to any disclaimer, the term of this patent is extended or adjusted under 35 U.S.C. 154(b) by 630 days.

(21) Appl. No.: 10/288,462

(22) Filed: Nov. 6, 2002

(65) Prior Publication Data

US 2003/0113904 A1  Jun. 19, 2003

Related U.S. Application Data

(62) Division of application No. 09/953,884, filed on Sep. 18, 2001, now Pat. No. 6,482,637.

(60) Provisional application No. 60/301,136, filed on Jun. 28, 2001.

(51) Int. Cl.
*G01F 25/00* (2006.01)

(52) U.S. Cl. .............. 73/1.16; 435/303.1; 435/303.2; 73/1.35; 73/861; 73/861.04; 600/22

(58) Field of Classification Search .............. None
See application file for complete search history.

(56) References Cited

U.S. PATENT DOCUMENTS

| | | | | |
|---|---|---|---|---|
| 5,792,427 A | * | 8/1998 | Hugh et al. | 422/109 |
| 6,265,210 B1 | * | 7/2001 | Silley et al. | 435/303.1 |
| 6,465,244 B1 | * | 10/2002 | Annable et al. | 435/303.2 |

* cited by examiner

*Primary Examiner*—David Redding
(74) *Attorney, Agent, or Firm*—Baker & Hostetler LLP

(57) ABSTRACT

Methods and apparatus for rapid gas recovery in a controlled gas atmosphere enclosure, which are particularly suited for maintaining incubator gas concentration levels, include the formulation of algorithms utilized for this purpose. The algorithms are included in the firmware for an embedded controller and operate gas solenoids that have inputs defined as specific gases at a defined pressure. An application of the rapid gas recovery method and apparatus to incubators is also disclosed.

4 Claims, 21 Drawing Sheets

(ENHANCEMENT MODE ONLY)

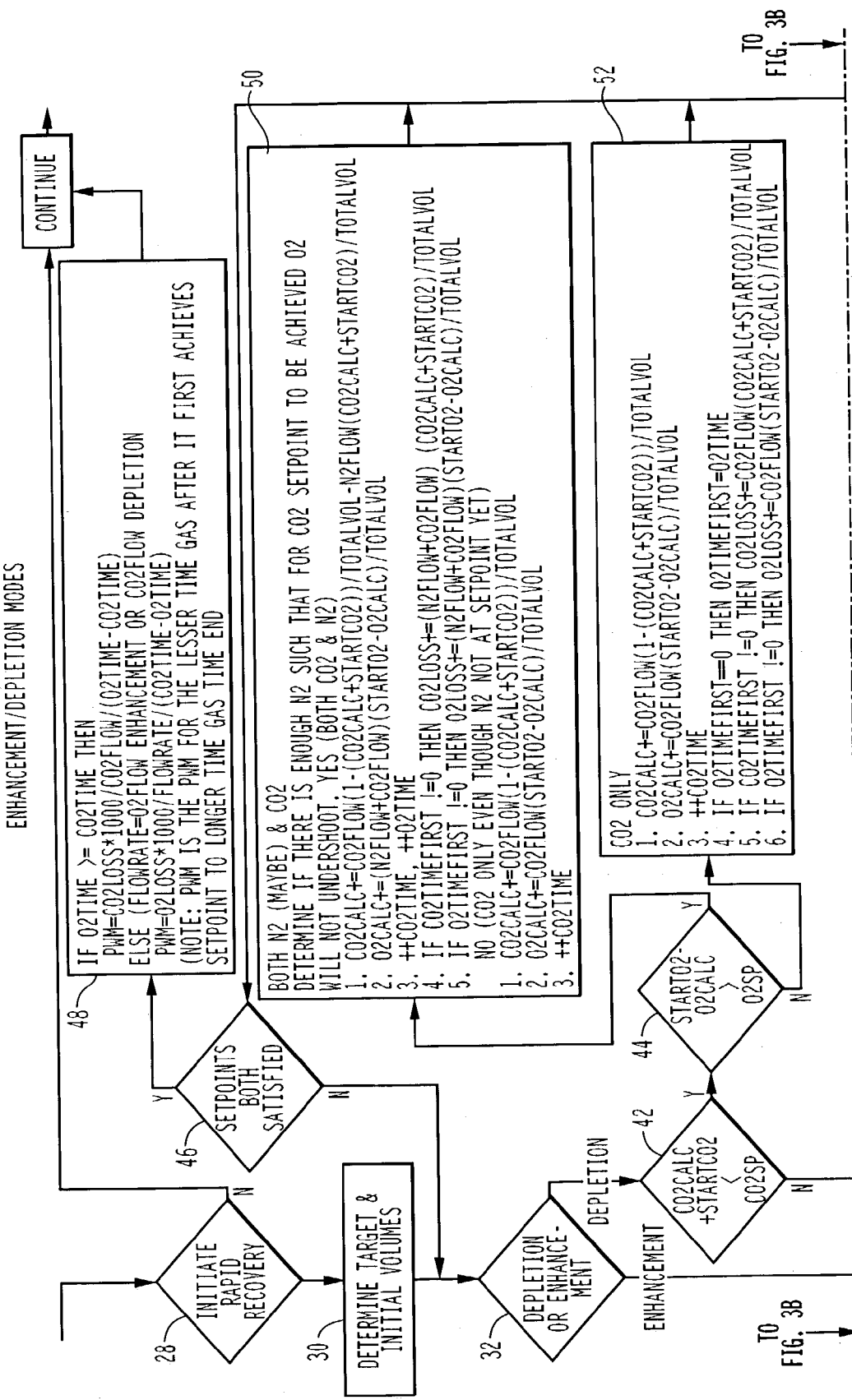

FIG. 5

CAB VOL 164.26

| | START% | STARTVOL | TARG% | TARGVOL | TIME | RRPWM | VOL AT END | % AT END | %DIF | MAX OR MIN |
|---|---|---|---|---|---|---|---|---|---|---|
| CO2 FLOW 0.0497 | 0.3 | 0.49278 | 10 | 16.426 | 365 | 14 | 16.49858 | 10.04419 | 0.044186 | 16.49858 |
| O2 FLOW 0.0622 | 20.9 | 34.3303 | 5 | 8.213 | 3175 | 0 | 8.205093 | 4.995186 | -0.004814 | 8.205093 / 8.205093 |

RAPID RECOVERY - DEPLETION

Graph: VOLUME (L) vs TIME (SEC), showing CO2VOL and O2VOLN2 curves.

| TIME | CO2VOL | O2VOLN2 |
|---|---|---|
| 0 | 0.493 | 34.330 |
| 1 | 0.542 | 34.307 |
| 2 | 0.591 | 34.284 |
| 3 | 0.641 | 34.260 |
| 4 | 0.690 | 34.237 |
| 5 | 0.739 | 34.214 |
| 6 | 0.788 | 34.190 |
| 7 | 0.837 | 34.167 |
| 8 | 0.886 | 34.144 |
| 9 | 0.936 | 34.121 |
| 10 | 0.985 | 34.097 |
| 11 | 1.034 | 34.074 |
| 12 | 1.083 | 34.051 |
| 13 | 1.131 | 34.028 |
| 14 | 1.180 | 34.005 |
| 15 | 1.229 | 33.981 |
| 16 | 1.278 | 33.958 |
| 17 | 1.327 | 33.935 |
| 18 | 1.376 | 33.912 |
| 19 | 1.424 | 33.889 |
| 20 | 1.473 | 33.866 |
| 21 | 1.522 | 33.843 |
| 22 | 1.570 | 33.820 |
| 23 | 1.619 | 33.797 |
| 24 | 1.668 | 33.774 |
| 25 | 1.716 | 33.751 |
| 26 | 1.765 | 33.728 |
| 27 | 1.813 | 33.705 |
| 28 | 1.861 | 33.682 |
| 29 | 1.910 | 33.659 |

DEPLETION

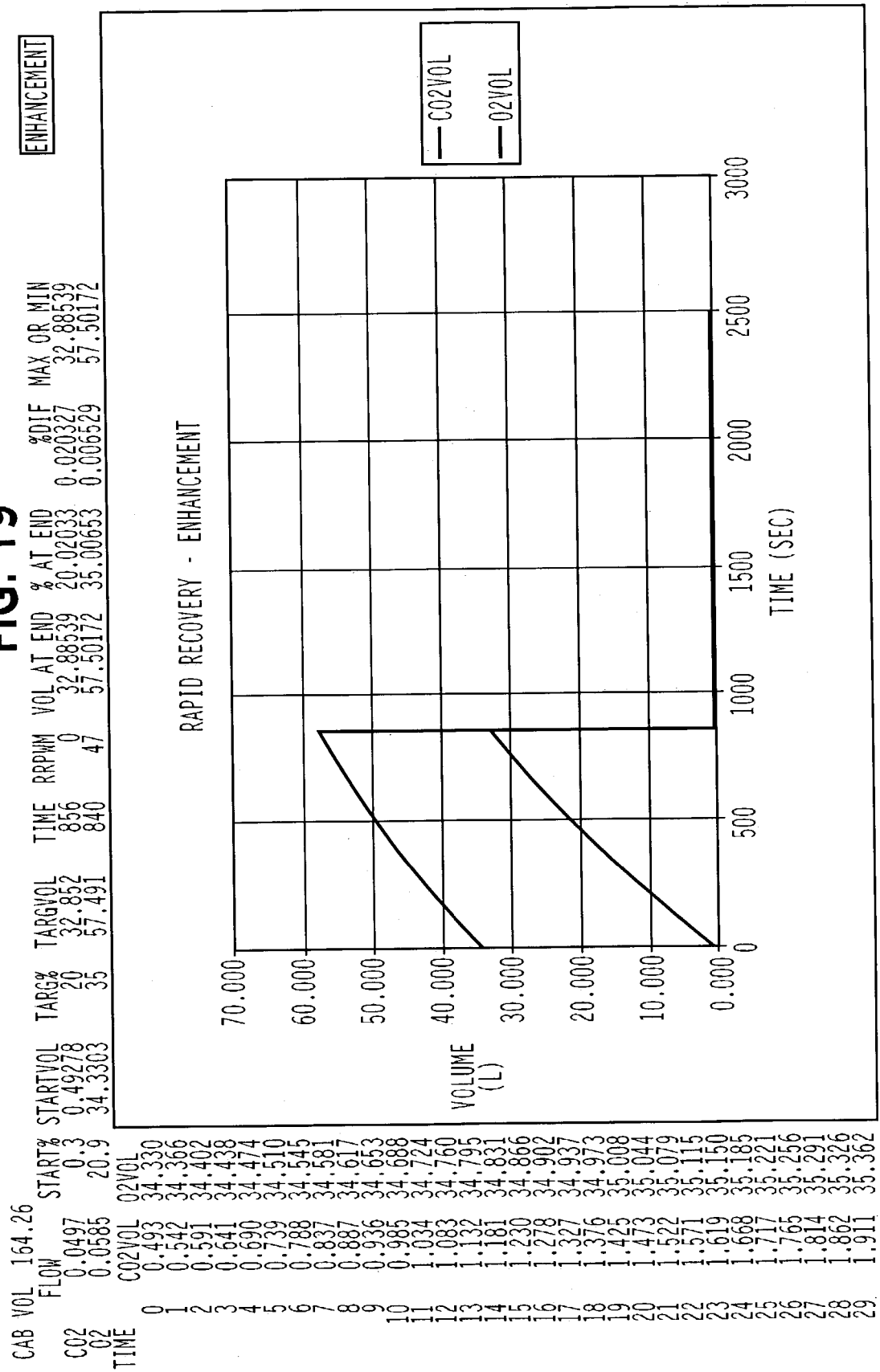

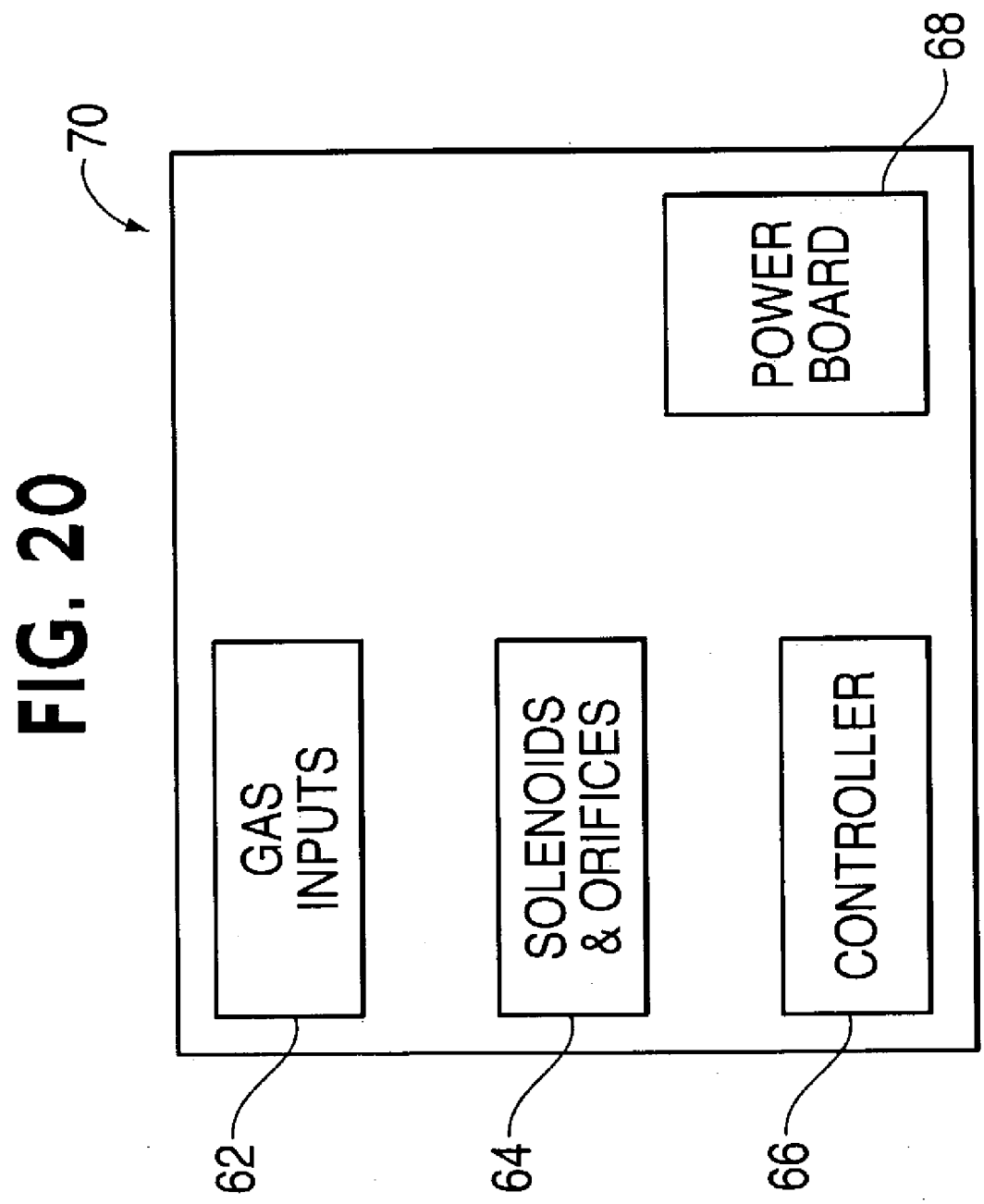

RAPID GAS RECOVERY IN AN INCUBATOR SYSTEM

PRIORITY

This application is a divisional of and claims priority to the pending application Ser. No. 09/953,884 entitled, "Rapid Gas Recovery in an Incubator System", filed Sep. 18, 2001, now U.S. Pat. No. 6,482,637 which claims priority to Provisional Application No. 60/301,136, filed Jun. 28, 2001, the disclosure of which is incorporated herein by reference.

FIELD OF THE INVENTION

The present invention relates generally to controlled gas atmosphere enclosures. More particularly the present invention concerns such enclosures for laboratory use, such as the growth of biological cultures. The present invention relates particularly to rapid gas recovery methods and apparatus in an incubator system.

BACKGROUND OF THE INVENTION

There are a number of commercial applications for controlled gas atmosphere enclosures. For example, electrical components and circuits are often tested in enclosures at a selected temperature and/or relative humidity for a period of time. Another common application for controlled atmosphere enclosures is the growth of biological cultures in the laboratory. As will be discussed herein with regard to a particular embodiment, the present invention may be advantageously employed in connection with a controlled gas atmosphere incubator in which a chamber for biological cultures is heated and in which the atmosphere of the chamber is controlled as to one or more constituent gases and/or the relative humidity.

A typical incubator of the foregoing type includes a generally cubical outer housing made up of five insulated walls (top, bottom, left side, right side, and rear) and an insulated front door. The door is mounted on hinges on the front of one of the side walls and may be opened to permit access to the interior of the incubator. When the door is closed, it is suitably sealed about its periphery to the housing walls to form the sixth wall of the housing. The incubator chamber, in which biological cultures are grown, is formed by inner walls, inside the insulated outer walls, and typically includes shelves upon which culture containers are placed. The shelves are carried by suitable shelf supports inside the chamber.

Most incubators of this type are either water jacket incubators or forced draft incubators. In a water jacket incubator the inner chamber is heated to the desired temperature by a sealed jacket of water surrounding the five fixed sides of the incubator chamber. The water jacket lies between the chamber wall and the insulated housing walls and is heated by heating elements in thermal contact with the water in the water jacket. Due to the thermal conductivity of water, the heat from the individual heating elements is relatively evenly dispersed over the water in the water jacket, providing even heating of the chamber. Such even heating is desirable in order to provide a uniform temperature for the biological cultures in different areas within the chamber and in order to prevent "cold spots" on the inner chamber wall upon which condensation can form.

Although the heating of the chamber walls in a water jacket incubator is substantially uniform, the chamber atmosphere will stratify thermally if the chamber atmosphere is undisturbed. When such stratification occurs, the temperature of the chamber atmosphere is greater at the top of the chamber than at the bottom of the chamber. In addition, if a constituent gas concentration is maintained in the chamber, such as a particular $CO_2$ level, the constituent gas will also stratify within the chamber atmosphere. Consequently, it is desirable to maintain a certain rate of flow within the chamber to assure uniformity of temperature and of constituent gases. In order to do this, typically a portion of the chamber is separated from the main chamber area by a wall to define a duct extending, for example, along a side of the chamber. A small blower or fan is placed in the duct and the chamber atmosphere is circulated, such as from a duct inlet in the upper portion of the chamber to a duct outlet in a lower portion of the chamber.

In a forced draft incubator, the inner chamber walls are insulated from the outer housing walls by a layer of insulation inside the housing walls. However, in this case there is no water jacket interposed between the insulated outer walls and the inner chamber walls. To obtain heating of the chamber in a forced draft incubator, some type of duct, such as described above, is typically provided within the chamber, and a fan and a heating element are mounted in the duct. As the fan circulates air from the main chamber area through the duct, the circulated chamber atmosphere is heated by the heating element. In order to heat the chamber atmosphere substantially uniformly, and to the desired temperature, considerably greater air flow is required than in the case of a water jacket incubator.

In a typical forced draft incubator, or water jacket incubator, if a constituent gas in the atmosphere of the incubator chamber is to be maintained at a particular level, a probe is introduced into the chamber, perhaps within the duct through which the chamber atmosphere circulates. In the case of $CO_2$, for example, a $CO_2$ sensor is introduced into the incubator chamber to measure the concentration of $CO_2$ therein. A source of $CO_2$ is then coupled to the interior of the chamber through a controlled valve, with an automatic control system actuating the valve as required to maintain the $CO_2$ concentration in the chamber at a selected level.

The humidity in a forced draft incubator is also often controlled. Rather than introducing steam or water into the incubator chamber as may be done in the case of a water jacket incubator, in a forced draft incubator quite often a pan of water is placed upon the floor of the incubator chamber, and the recirculated chamber atmosphere is directed out of the bottom of a duct across the surface of the water in the pan. Due to the higher recirculation rates in a forced draft incubator, appropriate humidification of the chamber is obtained.

In either a forced draft or a water jacket incubator, sensors such as for $CO_2$ or humidity have typically been located within the chamber atmosphere itself, although perhaps within a recirculation duct, as earlier described. Such sensors in the chamber are subject to the chamber atmosphere, and a sensor can fail or suffer performance degradations due to contaminants or the accumulation of a coating on the sensor. The presence of such sensors in the incubator chamber itself also makes cleaning of the chamber interior more difficult. In fact, the very existence of a duct or the like for the circulation of the chamber atmosphere within the chamber introduces difficulties in cleaning the chamber.

The recirculation of the chamber atmosphere, such as through a duct, in either type of incubator presents yet another problem, that of potential contamination of biological cultures within the chamber. Contaminants such as mold spores are almost invariably present in the chamber atmosphere and may be directed by the recirculatory air flow into the biological culture containers. Culture contamination problems are exacerbated by the higher air flows required in forced draft incubators.

Higher air flow rates involved in forced draft incubators have a further disadvantage in that the higher flow rates tend to dry out biological culture media. To a large degree, the necessity of offsetting this desiccation results in the requirement for humidity control in forced draft incubators. In such incubators, a relatively high humidity is maintained so that the drying effect of the gas flow is ameliorated.

Incubators are typically used for growing cultures in a controlled environment wherein both temperature and atmospheric gas concentration are maintained at selected levels. For certain applications it is highly desirable to have both temperature and gas concentrations maintained within strict tolerances while still allowing easy access to the incubator chamber for adding or removing items to and from the chamber or for inspecting the contents of the chamber. Control of environmental variables is desirable to maintain accuracy and reproducability of incubation results.

Therefore, it would be desirable to provide an incubator having accurate gas concentration control with fast recovery of gases (typically $CO_2$ combined with $O_2$ or $N_2$) by determination of the total gas volume required including gas loss due to same gas injection and gas loss due to other gas injection.

SUMMARY OF THE INVENTION

The foregoing needs have been satisfied to a great extent by the present invention which, in one aspect, includes the formulation of algorithms utilized for gas control in an incubator system. The algorithms are included in the firmware for an embedded controller and operate gas solenoids that have inputs defined as specific gases (e.g., $CO_2$ alone or in combination with $O_2$ or $N_2$) at a defined pressure. The flow rate is then estimated and the needed volume for a specific gas is determined by numerically solving for the time the solenoid should be on. The algorithm adjusts for sensor response time and then a steady state algorithm ensues to bring the gas level to the final desired level and maintain gas levels due to normal loss.

It is accordingly an object of the present invention to provide an improved incubator control system which accurately maintains environmental levels within an incubator chamber.

There has thus been outlined, rather broadly, the more important features of the invention in order that the detailed description thereof that follows may be better understood, and in order that the present contribution to the art may be better appreciated. There are, of course, additional features of the invention that will be described below and which will form the subject matter of the claims appended hereto.

In this respect, before explaining at least one embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein, as well as the abstract, are for the purpose of description and should not be regarded as limiting.

As such, those skilled in the art will appreciate that the conception upon which this disclosure is based may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

BRIEF DESCRIPTION OF THE DRAWINGS

FIG. 5 is a Rapid Recovery Graph of $O_2$ & $CO_2$ from Normal Conditions to $O_2$=5%, $CO_2$=10%.

FIG. 19 is a Rapid Recovery Graph of $O_2$ & $CO_2$ from Normal Conditions to $O_2$=35%, $CO_2$=20%.

FIG. 20 is a block diagram of the component structure of an embodiment of the present invention.

DETAILED DESCRIPTION OF PREFERRED EMBODIMENTS OF THE INVENTION

Figure 1:
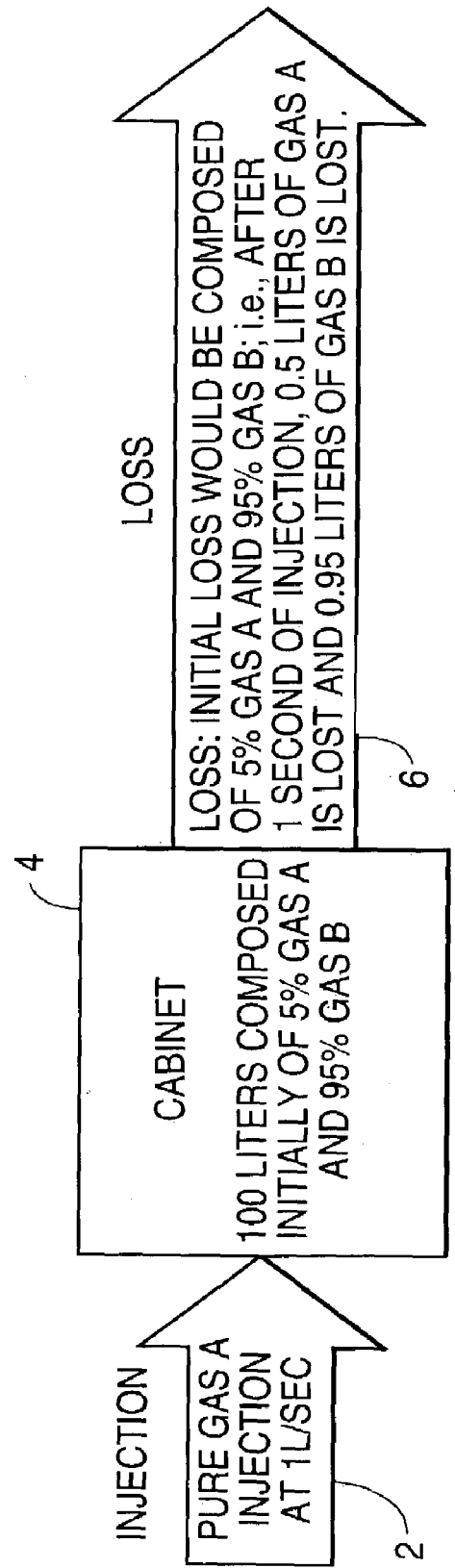
FIG. 1 is a Simplified Loss Model.

Referring to the figures, wherein like reference numerals indicate like elements, FIG. 1 demonstrates an example of the loss process in a cabinet caused by adding pure GasA 2 for one second. After this initial one second, the volume for GasA can be determined by knowing the original GasA volume 4, summing the added GasA, and finally subtracting the GasA loss 6, which in this case was due to a same gas injection. Similarly, GasB volume can be determined by knowing the original GasB volume 4 and losses that were incurred due to GasA injection 2. This is repeated until the running total for the GasA volume 4 reaches the setpoint. This loss model can easily be extrapolated for additional gasses. Note that the pressure in the cabinet is very near to atmospheric pressure and hence a correction for pressure can be ignored. Also there is a dependence on the time interval at which the running calculations are performed, the smaller the more accurate. For the example of the preferred embodiment described below, a one second interval was applied which also corresponds to the injection PWM period.

Algorithm 3 is most appropriate for the preferred embodiment, an incubator system. Algorithms 1 and 2 are appropriate for enhancement mode; i.e., both gases require the addition/injection of gas to achieve setpoint and no gas was purposefully purged by another gas to achieve setpoint. These algorithms can predict the loss that will occur when injecting gas into an enclosure that in not pressurized. The calculation can be summarized as follows:
1. Determine what qualifies for initiation of rapid gas recovery 8, 28 (ex. door opening greater than 20 seconds).
2. Determine the start and target volumes 10 for each gas.
3. Predict the total volume needed for the gas by iteratively adding injected gas and subtracting loss due to same gas injection and other gas injection(s) based on volumetric proportions 12–26.
4. Modify these times as required by other system specifications (there will be 3 slightly different algorithms discussed herein, depending on system requirements).

The first step is most likely specific to the system and should be equivalent to having gas concentrations that greatly deviate from a user setpoint(s) that need to be recovered. The second step is done via the microcontroller 66 which can read $O_2$ and $CO_2$ sensors (not shown) via an Analog to Digital Converter (not shown) and also provides a mechanism for the user to adjust the desired setpoint via an interface (not shown). The third step is where the algorithms become advantageous. At this point, the target volume is iteratively compared with the sum of the calculated volume and start volume including any losses 12–26. Next, volume changes are calculated by adding the product of the same gas flow rate and a time interval (in the preferred embodiment, a one second period is utilized), subtracting the product of the same gas flow rate and the same gas volumetric percentage, and then finally (if more than one gas is being injected, in the preferred embodiment, two gasses were used) subtracting the product of the other gas flow rate and the same gas volumetric percentage. Additional gases could be accounted for at this stage as well.

Figure 2:
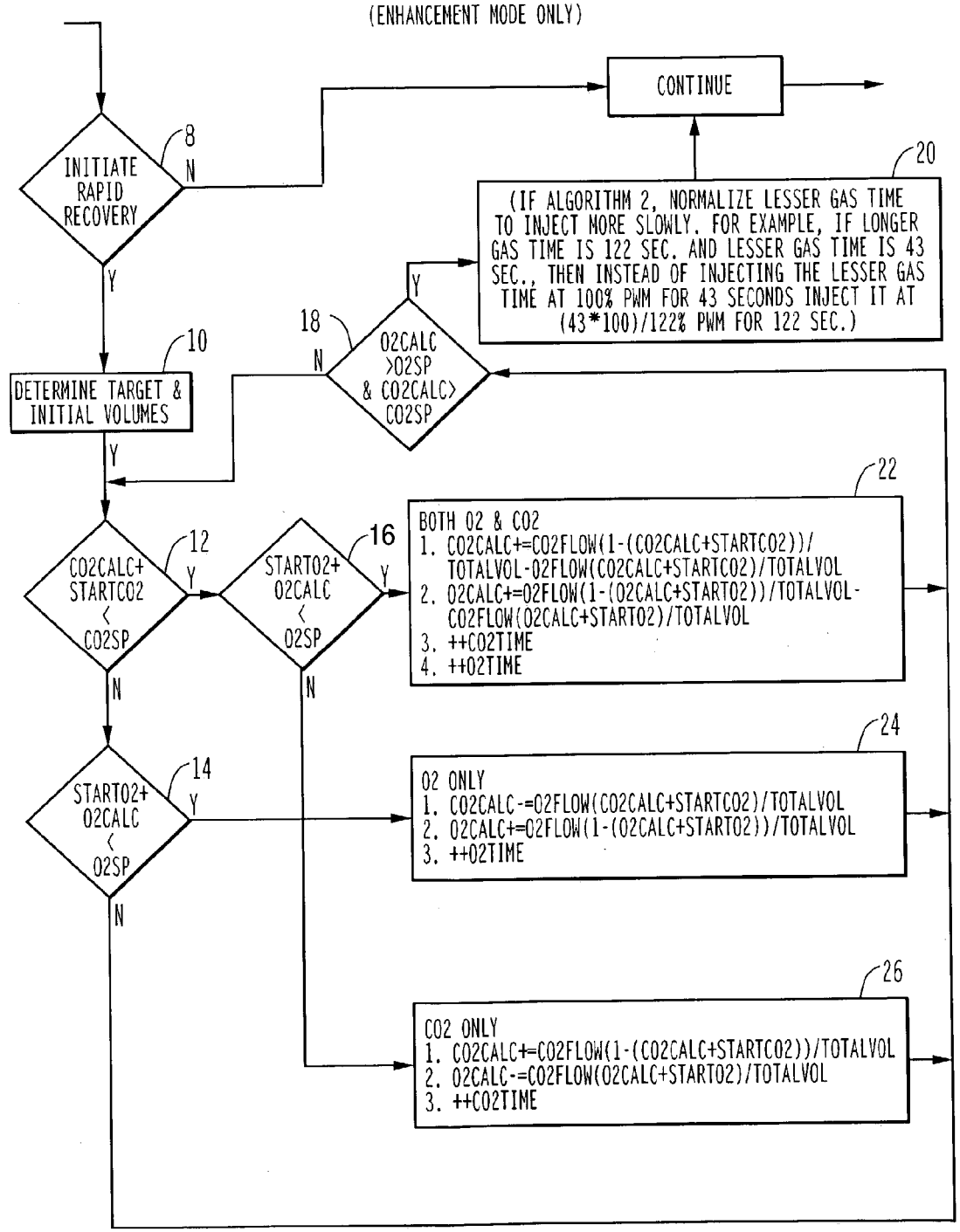
FIG. 2 is a Flowchart of Algorithms 1 and 2 of a preferred embodiment of the present invention.

Referring to FIGS. 2 & 20, wherein like reference numerals indicate like elements, Algorithm 1 continues this process until all gas volumes are satisfied (again, two gases in the example of the preferred embodiment). At this point, the times that the solenoid(s) 64 are required to be full on has been determined as each gas keeps a counter of the one second intervals it should be full on. Then the microcontroller 66 can activate the solenoid(s) 64 for the calculated times and expect to be at/or near the target volumes 10 when a time interval equivalent to the longest time gas calculation has elapsed. Notice that constant rechecking of the status 12–16; i.e., setpoint versus actual, is not required during rapid recovery 8 and there is a potential to conserve bandwidth of the embedded system 70. Algorithm 1 can cause an overshoot issue for some systems if the flow rates and/or the times calculated respectively differ significantly. In the extreme case (enhancement mode), the gas with the lesser time calculation 12–16, 22–26 will overshoot the user target setpoint 10. The remaining time that the other gas solenoid 64 is on removes the excess lesser time gas. There are a couple of approaches to address this issue. Algorithms 2–3 are other examples that can improve the overshoot issue.

Referring to FIG. 2, wherein like reference numerals indicate like elements, Algorithm 2 addresses overshoot by normalizing 18, 20 the lesser time gas(es) to the time calculated for the longest gas and then reducing the PWM of each lesser time gas solenoid 64 appropriately. In other words, the lesser time gases inject more slowly over the longest gas time. This could be done for multiple lesser time gases but only two gases were used in the example preferred embodiment and therefore only one lesser time gas was present. This too will result at the correct gas concentrations after a time equivalent to the longest gas time has elapsed. However, Algorithm 2 also presents a problem for the user if it is desired to achieve and maintain each gas setpoint as rapidly as possible for the given pressure/orifice combination.

Figure 3B:
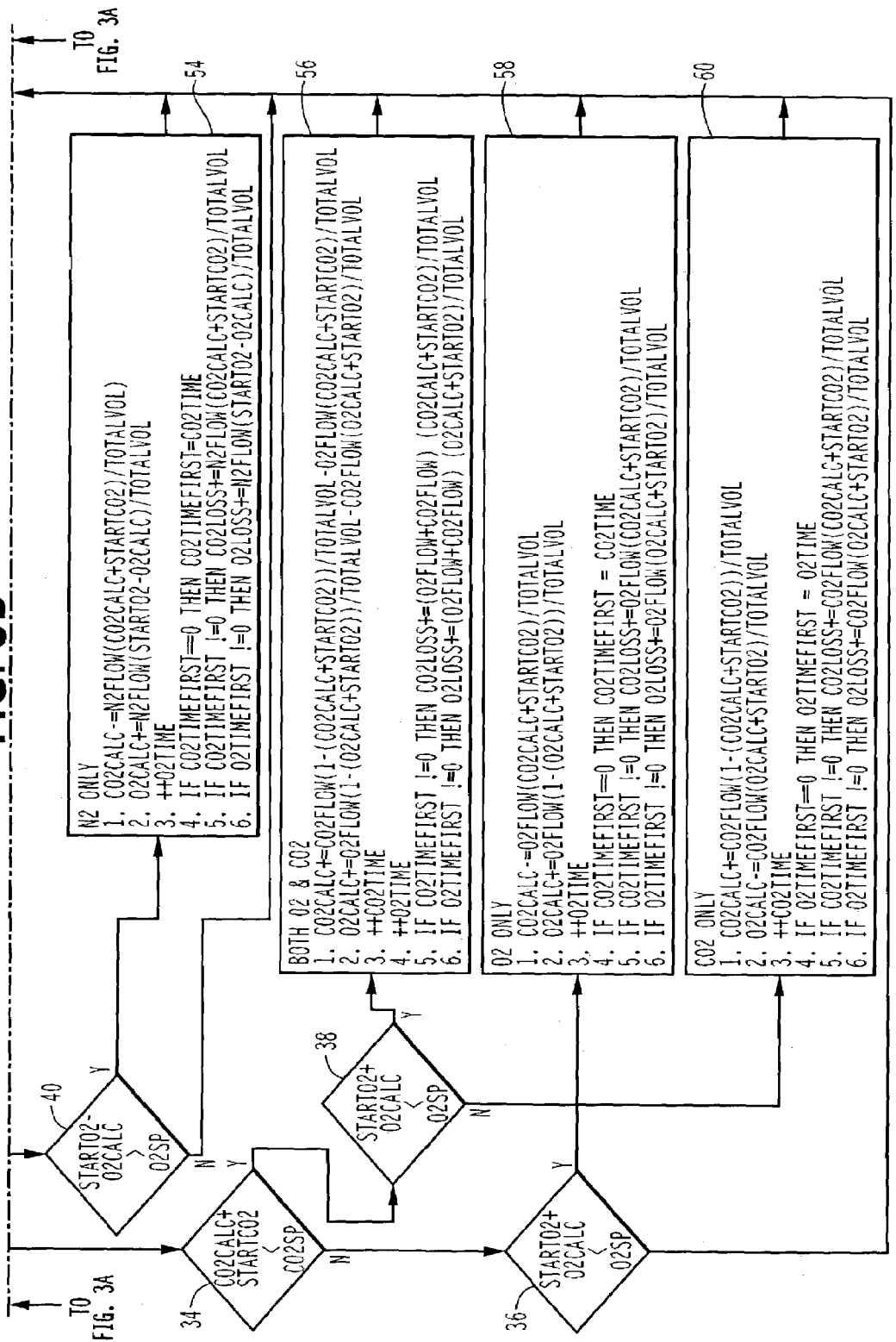
FIG. 3 is a Flowchart of Algorithm 3 of a preferred embodiment of the present invention.
Figure 4:
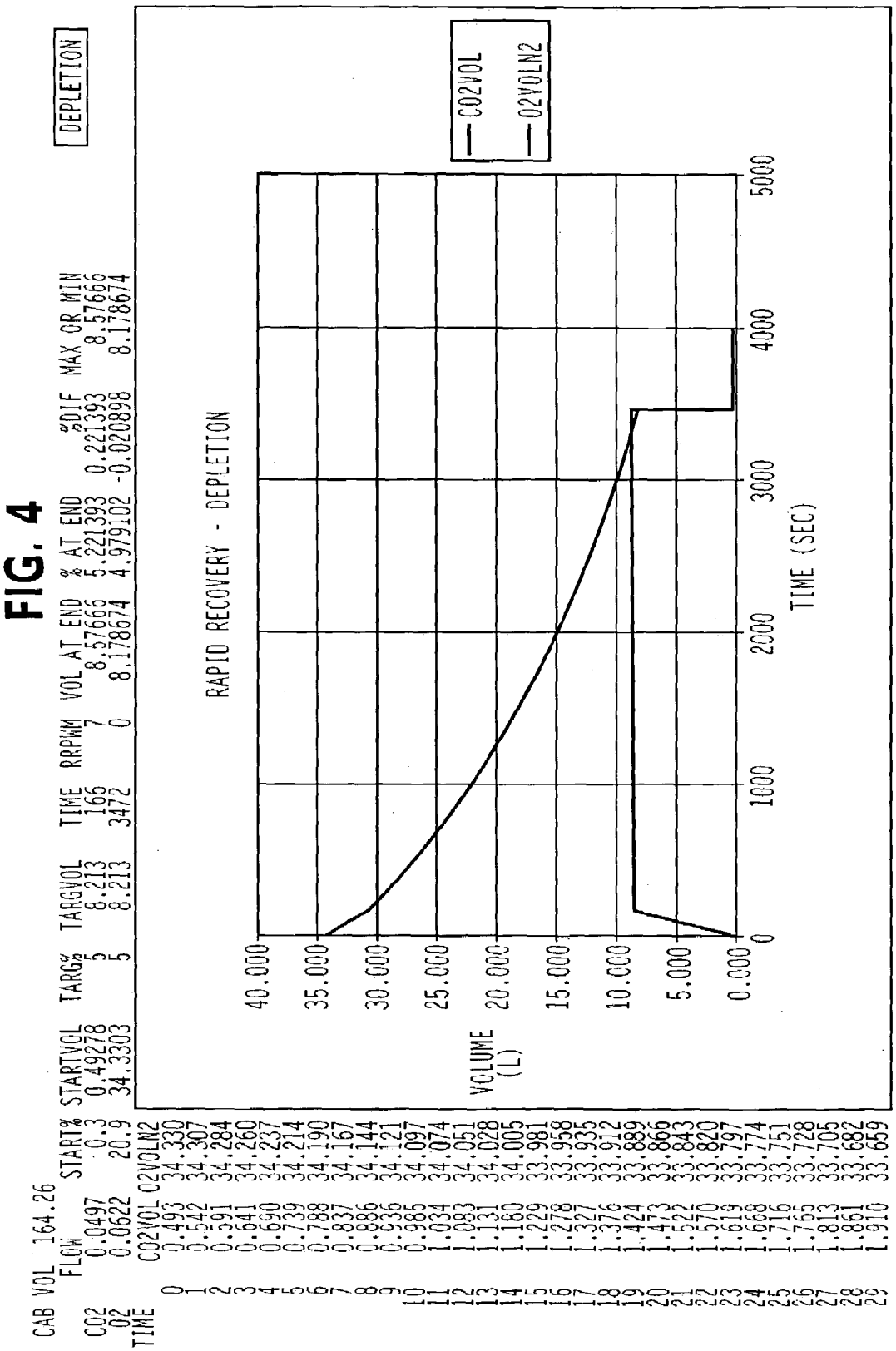
FIG. 4 is a Rapid Recovery Graph of $O_2$ & $CO_2$ from Normal Conditions to $O_2$=5%, $CO_2$=5%.
Figure 6:
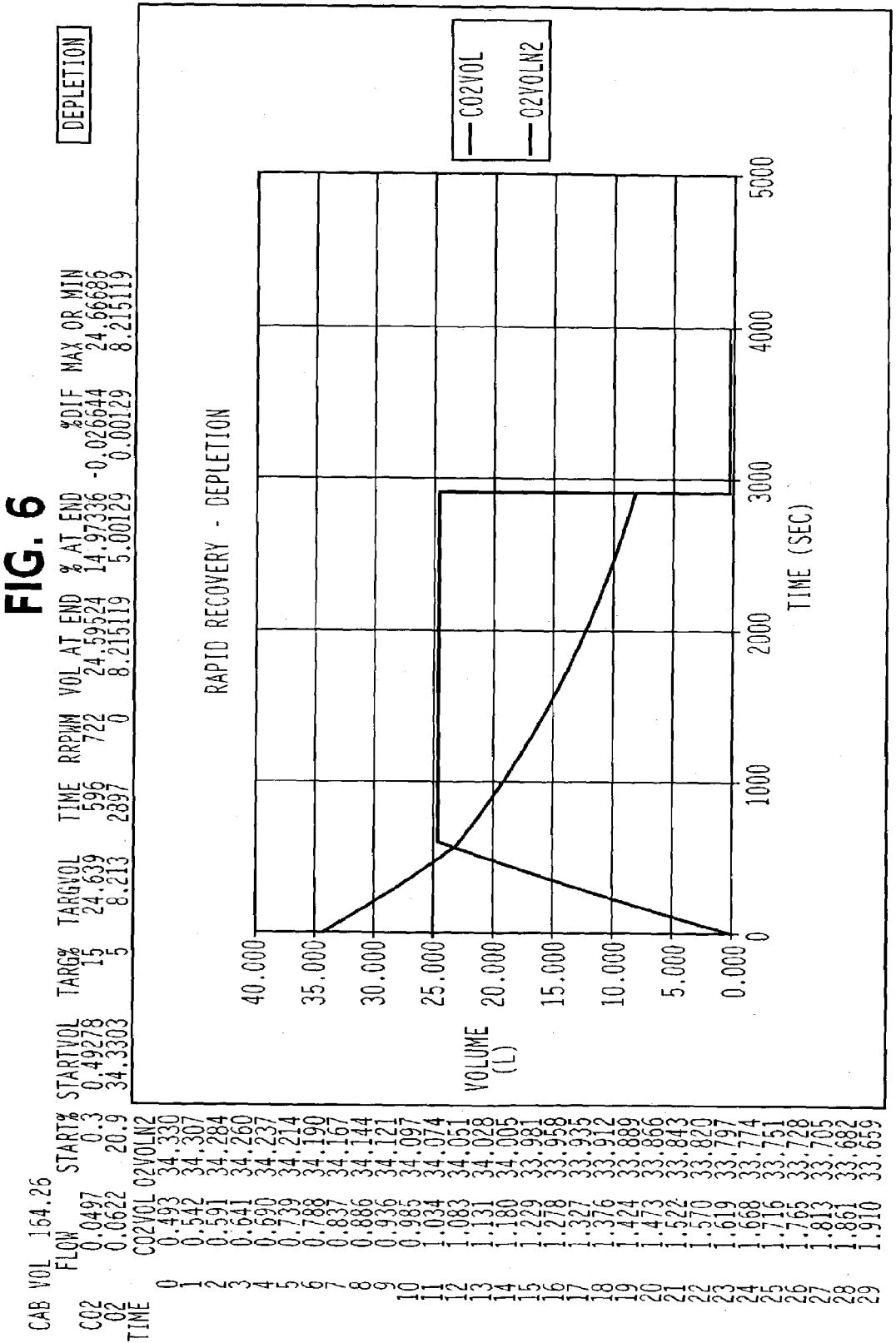
FIG. 6 is a Rapid Recovery Graph of $O_2$ & $CO_2$ from Normal Conditions to $O_2$=5%, $CO_2$=15%.
Figure 7:
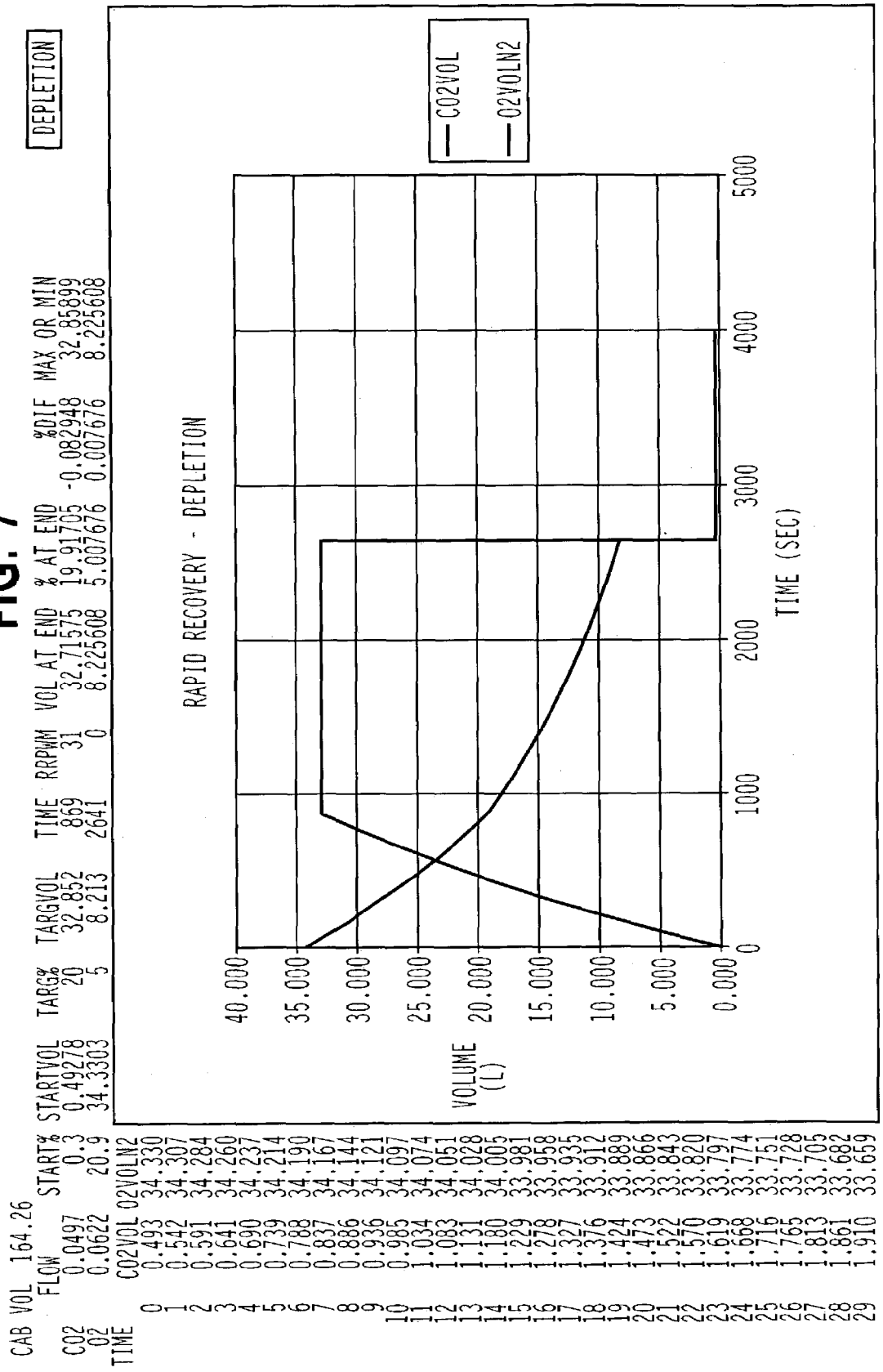
FIG. 7 is a Rapid Recovery Graph of $O_2$ & $CO_2$ from Normal Conditions to $O_2$=5%, $CO_2$=20%.
Figure 8:
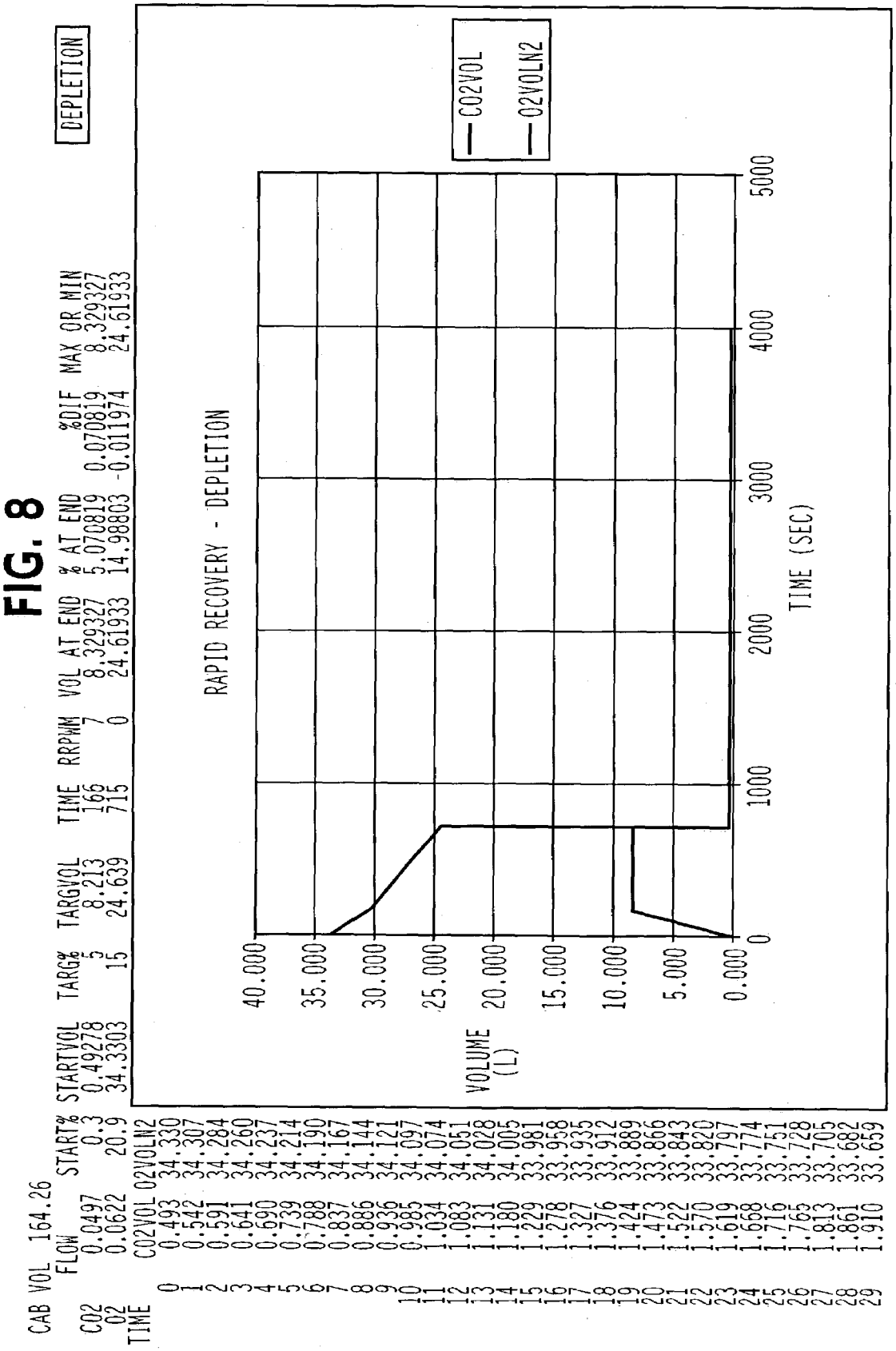
FIG. 8 is a Rapid Recovery Graph of $O_2$ & $CO_2$ from Normal Conditions to $O_2$=15%, $CO_2$=5%.
Figure 9:
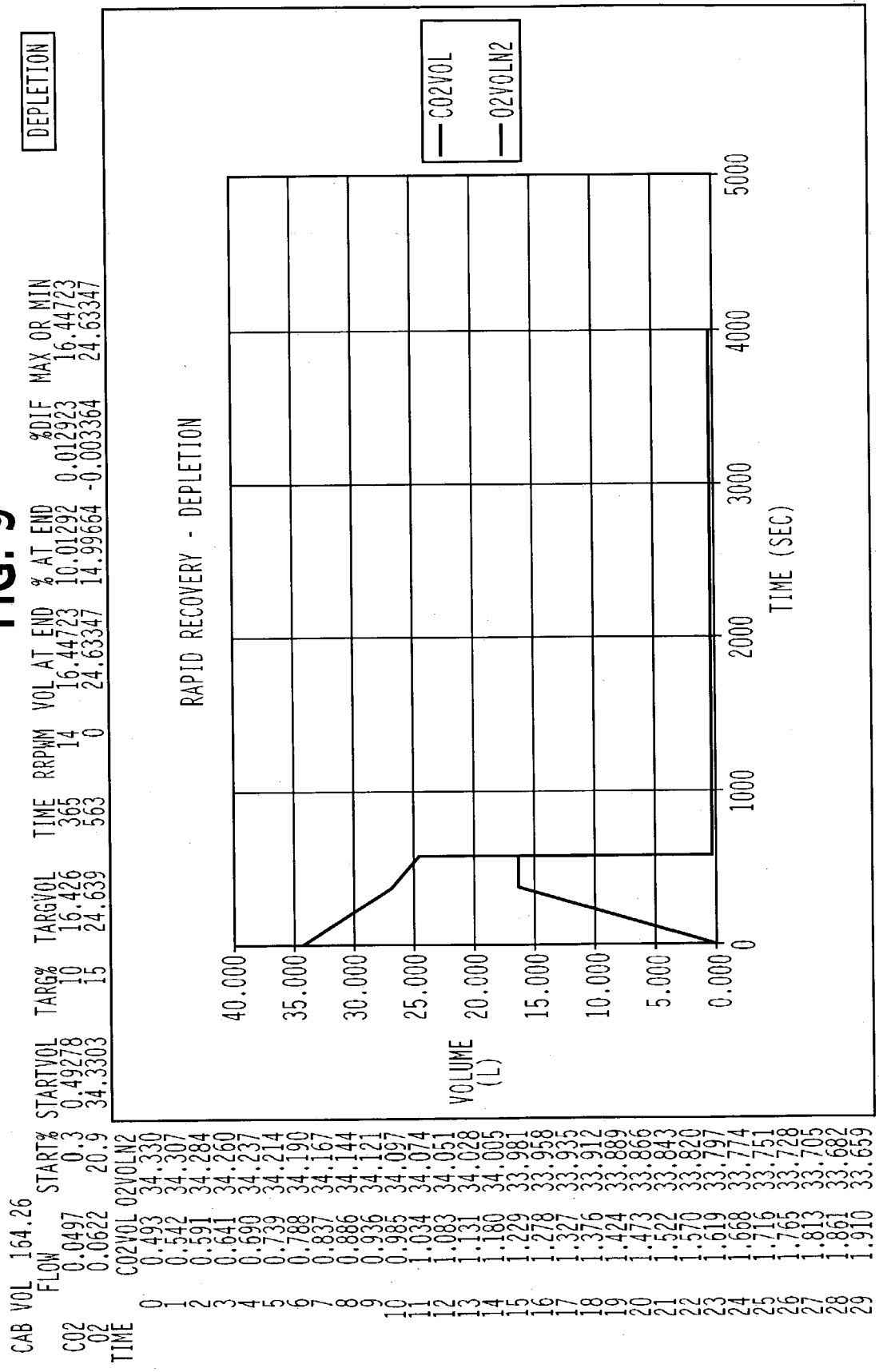
FIG. 9 is a Rapid Recovery Graph of $O_2$ & $CO_2$ from Normal Conditions to $O_2$=15%, $CO_2$=10%.
Figure 10:
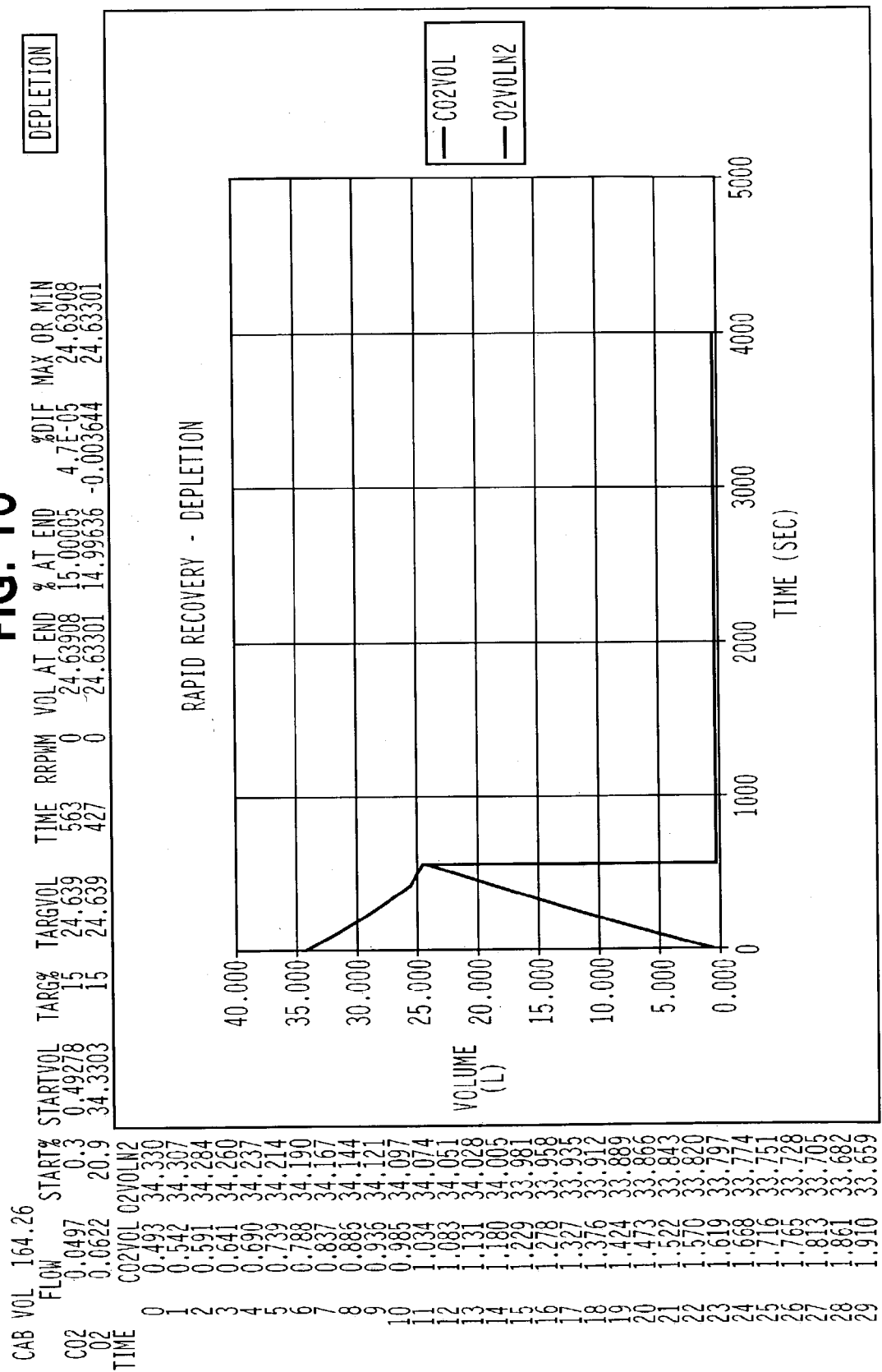
FIG. 10 is a Rapid Recovery Graph of $O_2$ & $CO_2$ from Normal Conditions to $O_2$=15%, $CO_2$=15%.
Figure 11:
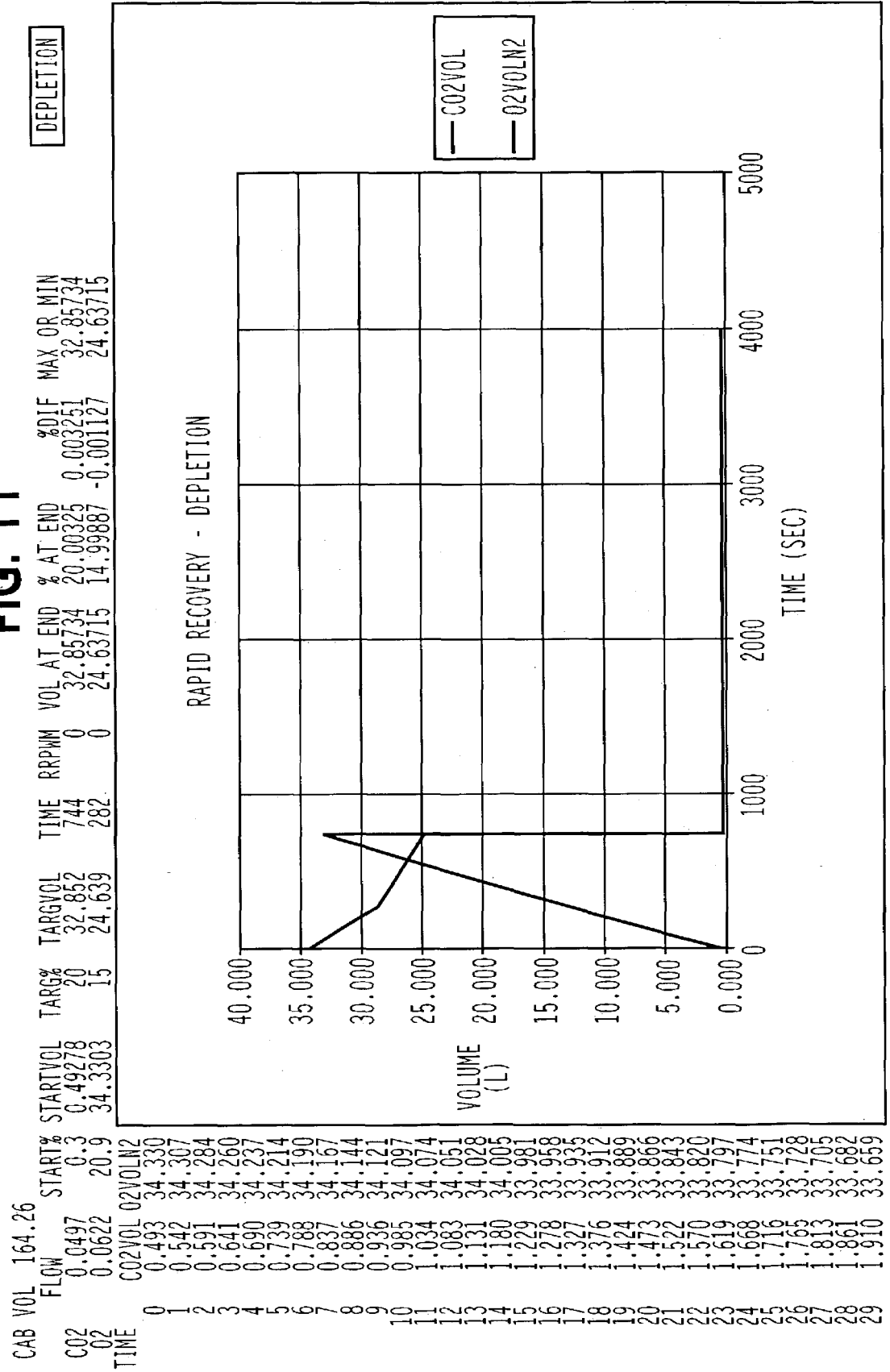
FIG. 11 is a Rapid Recovery Graph of $O_2$ & $CO_2$ from Normal Conditions to $O_2$=15%, $CO_2$=20%.
Figure 12:
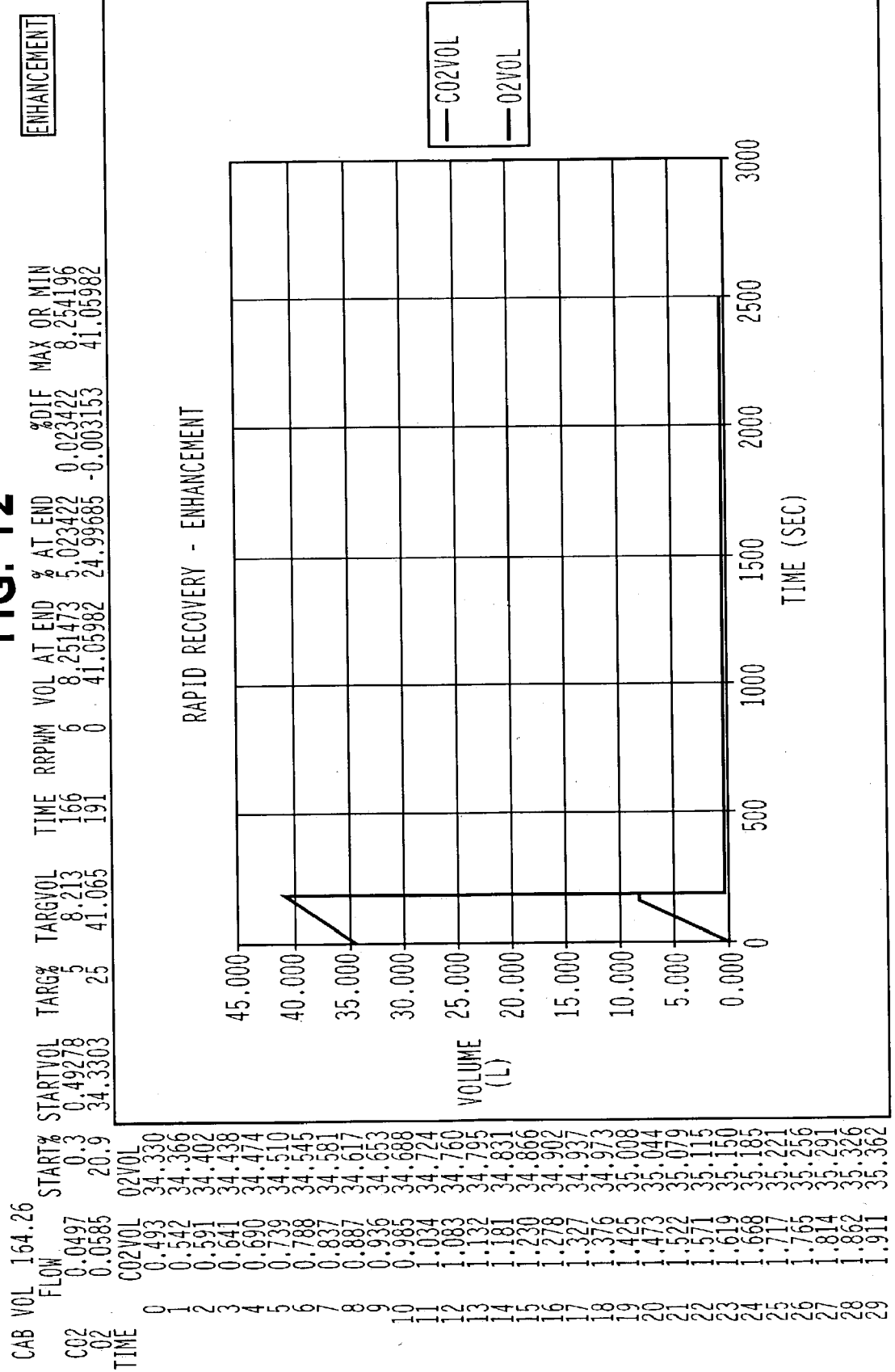
FIG. 12 is a Rapid Recovery Graph of $O_2$ & $CO_2$ from Normal Conditions to $O_2$=25%, $CO_2$=5%.
Figure 13:
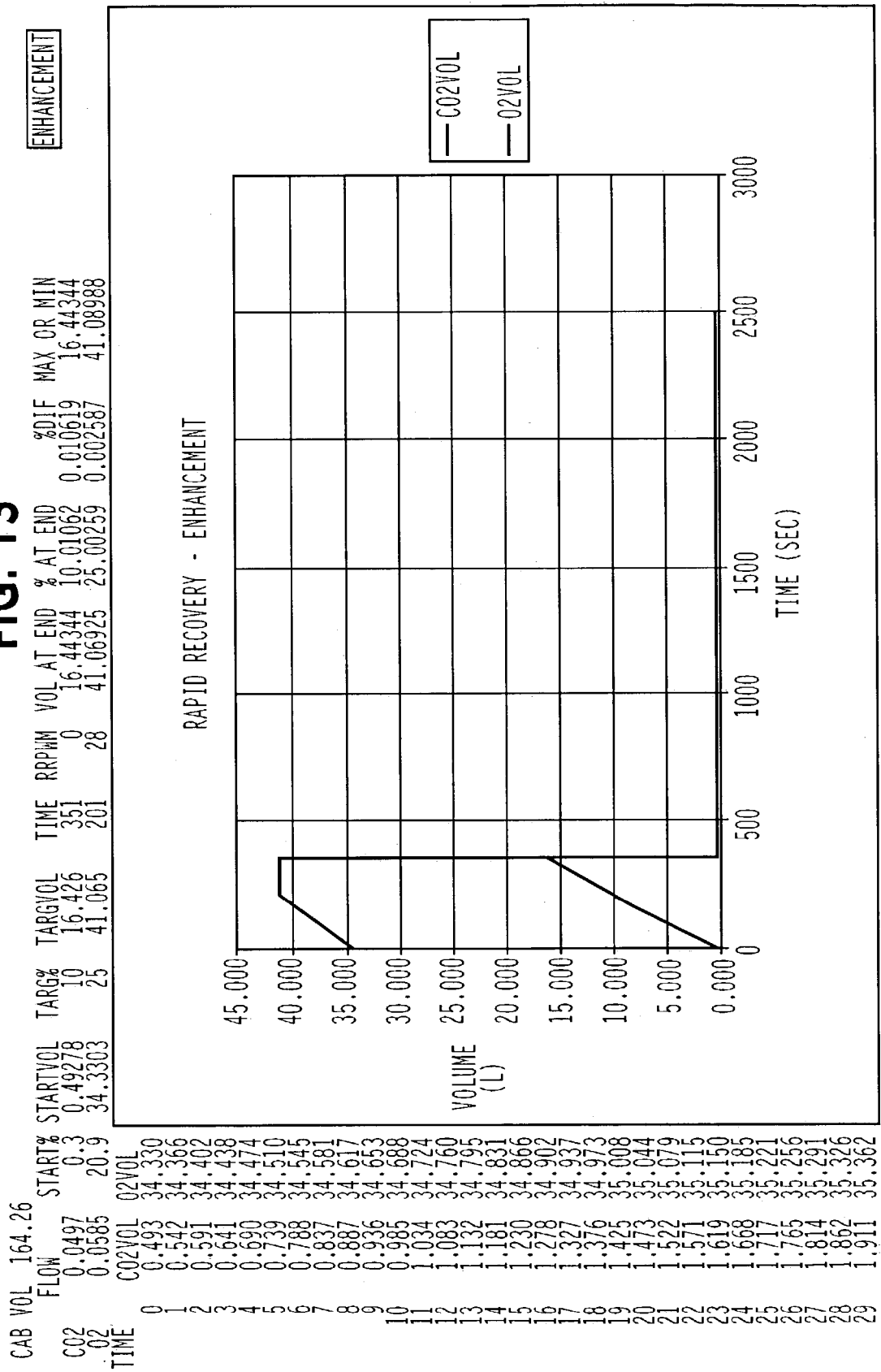
FIG. 13 is a Rapid Recovery Graph of $O_2$ & $CO_2$ from Normal Conditions to $O_2$=25%, $CO_2$=10%.
Figure 14:
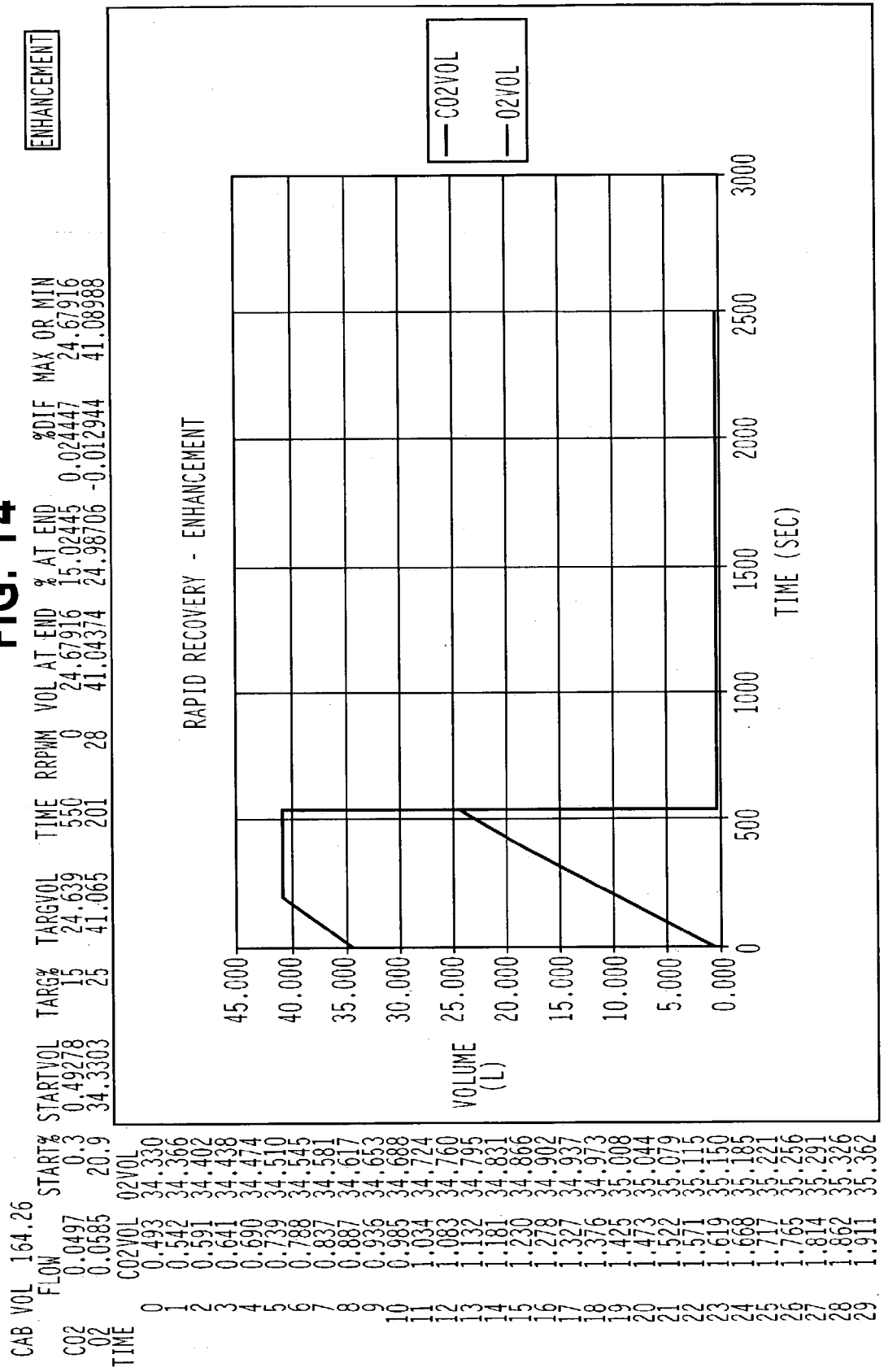
FIG. 14 is a Rapid Recovery Graph of $O_2$ & $CO_2$ from Normal Conditions to $O_2$=25%, $CO_2$=15%.
Figure 15:
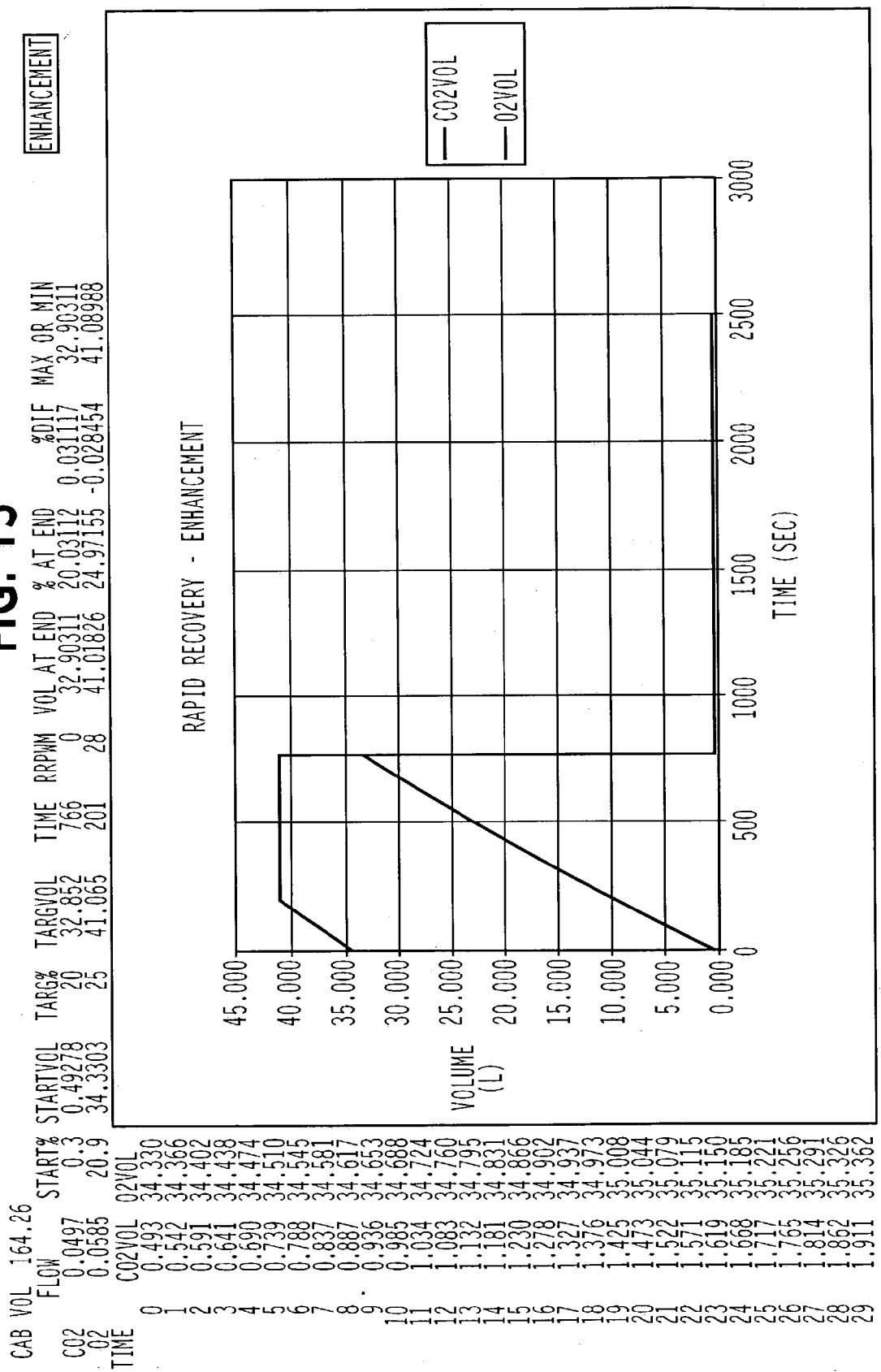
FIG. 15 is a Rapid Recovery Graph of $O_2$ & $CO_2$ from Normal Conditions to $O_2$=25%, $CO_2$=20%.
Figure 16:
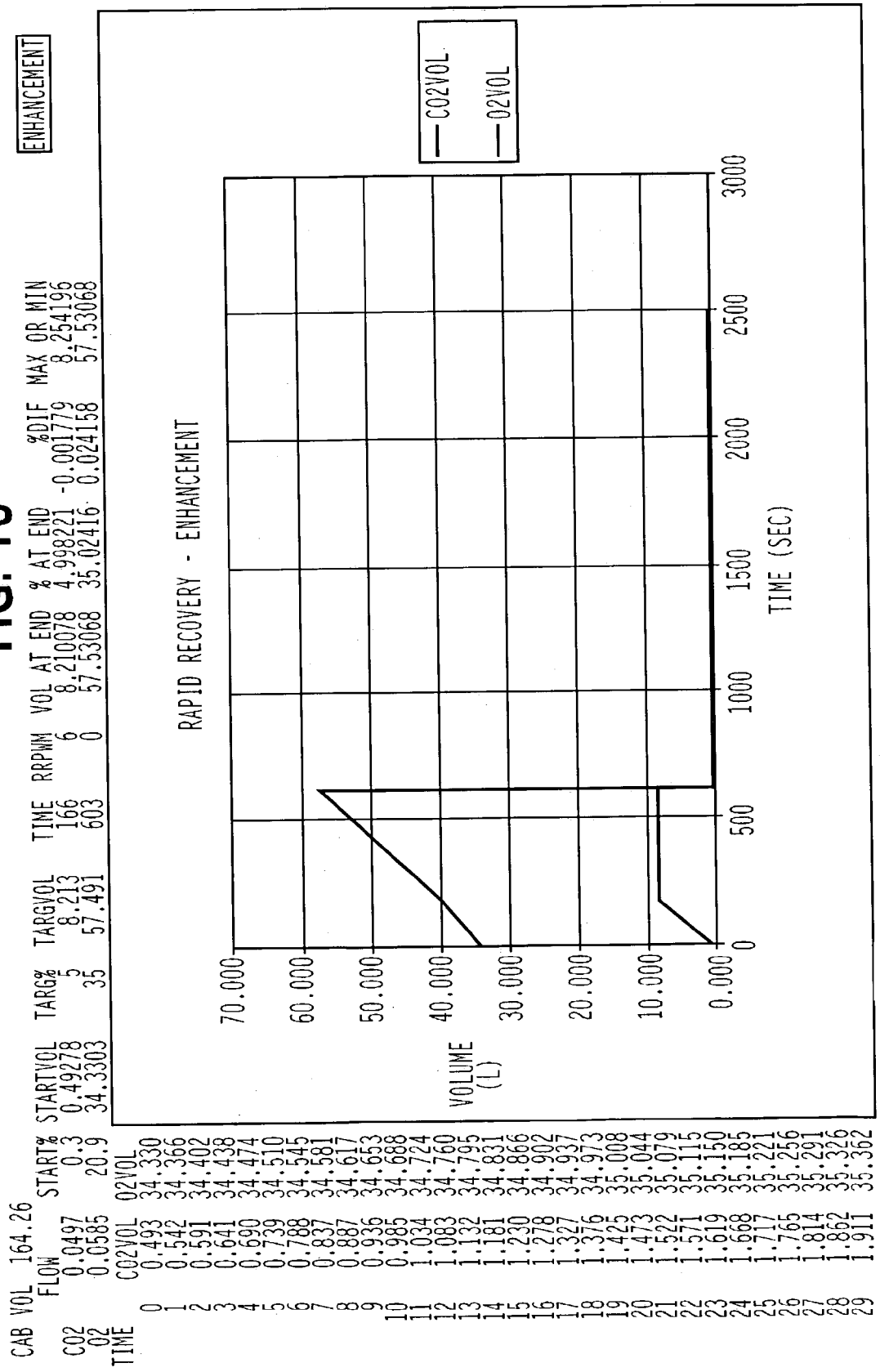
FIG. 16 is a Rapid Recovery Graph of $O_2$ & $CO_2$ from Normal Conditions to $O_2$=35%, $CO_2$=5%.
Figure 17:
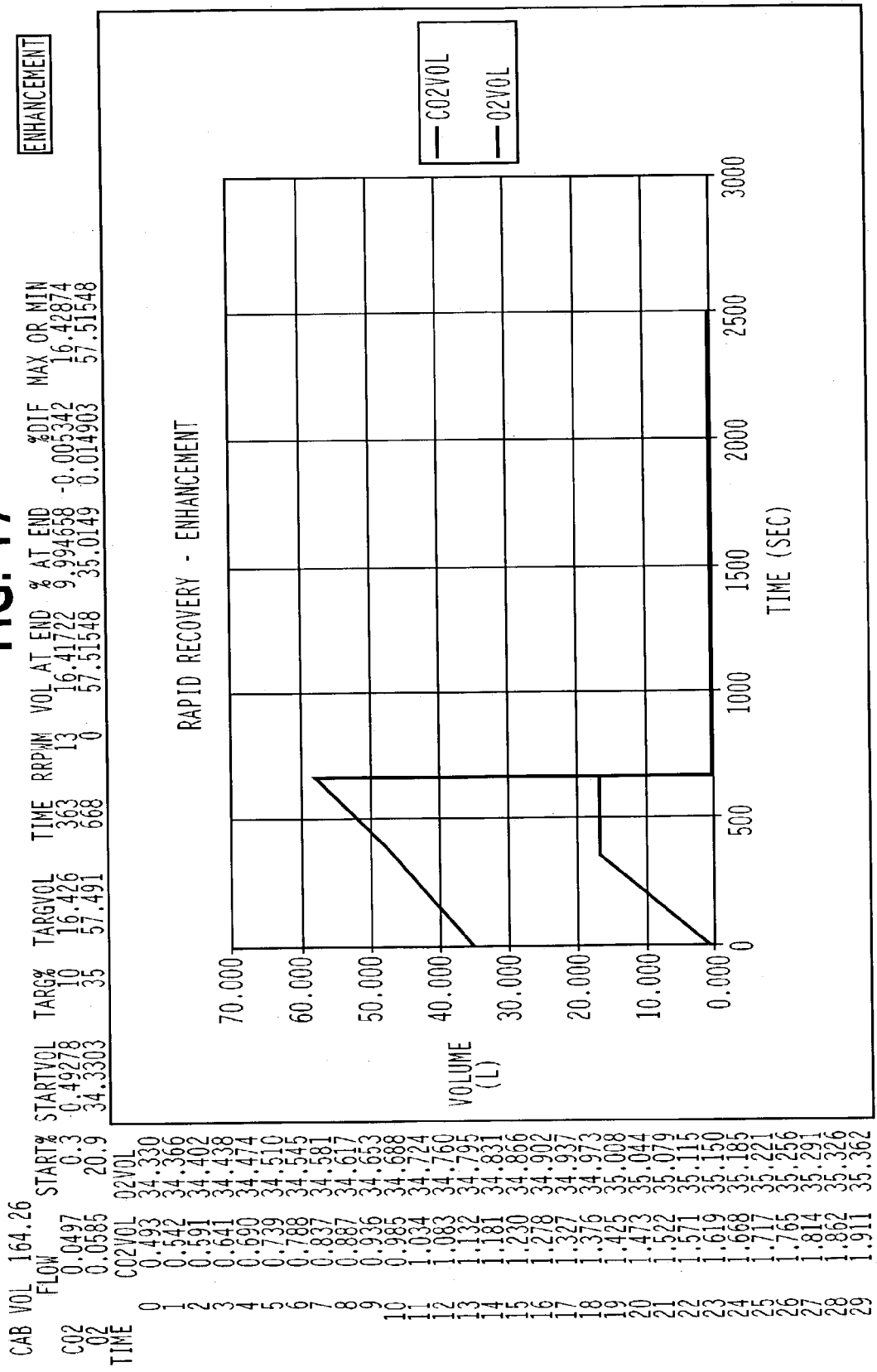
FIG. 17 is a Rapid Recovery Graph of $O_2$ & $CO_2$ from Normal Conditions to $O_2$=35%, $CO_2$=10%.
Figure 18:
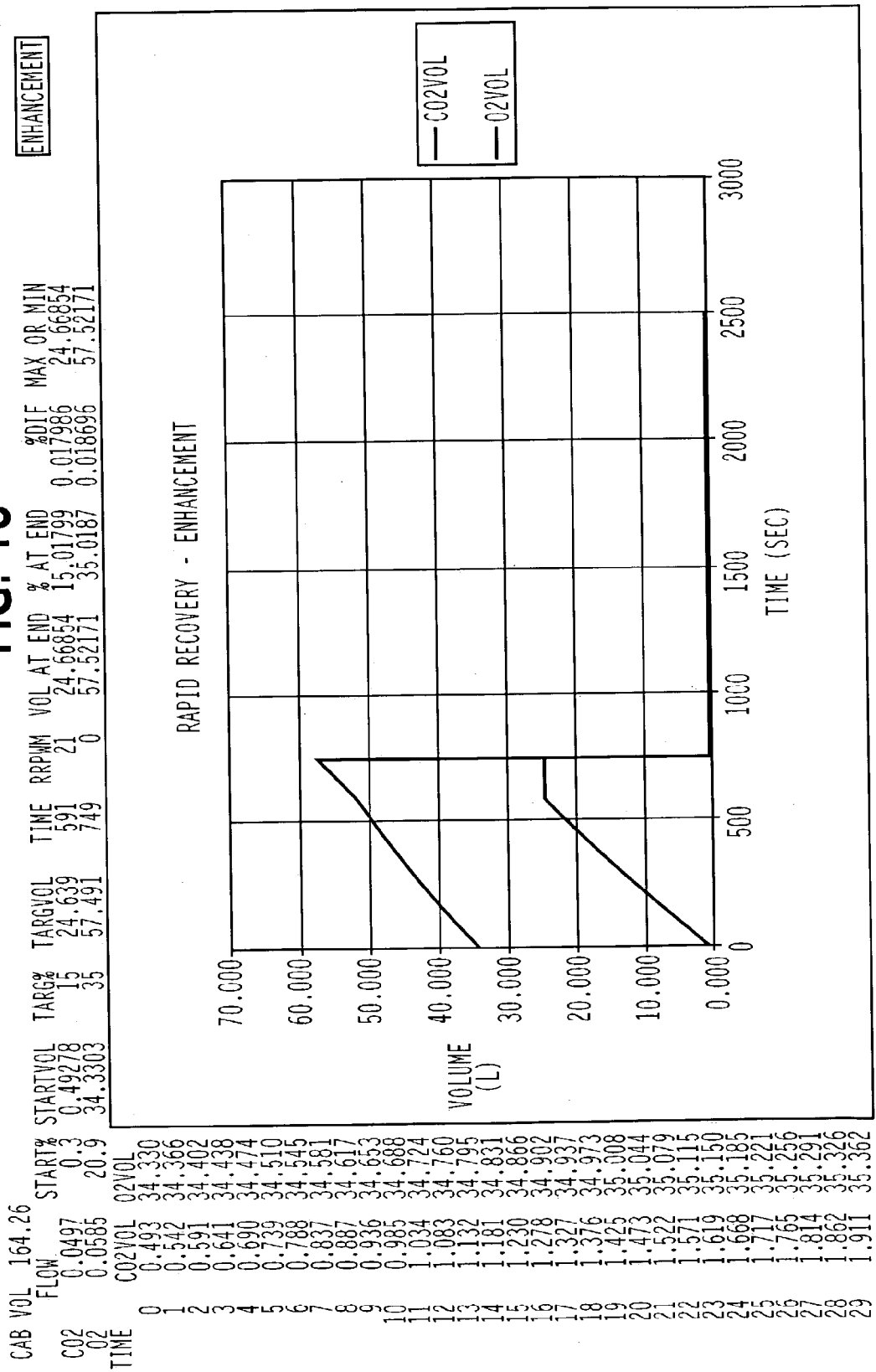
FIG. 18 is a Rapid Recovery Graph of $O_2$ & $CO_2$ from Normal Conditions to $O_2$=35%, $CO_2$=15%.

Referring to FIG. 3, Algorithm 3 leverages the predictive loss characteristics for all gases involved, allows for rapid gas recovery 28 for each gas, and minimizes bandwidth. It was developed specifically for the example of the preferred embodiment, a system of two gases, $O_2/N_2$ and $CO_2$, in which $O_2$ can run in depletion mode 30, 32, 40, 42, 44, 50, 52, 54 by purging with $N_2$, and $CO_2$ is always enhanced. It calculates the times at which one of the gases first achieves setpoint and then dynamically predicts the loss of that gas during the remaining time to the longest gas time. In this way, the lesser time gases (those with full on times less than the longest time) will rapidly achieve setpoint 46 and then utilize a calculated PWM 48 based on the predicted loss during the remaining time to the end of rapid gas recovery; i.e., the longest gas time, to compensate for losses attributed to continued longer time gas injection(s). Depletion is a special concern as the preferred embodiment uses $N_2$ to purge $O_2$ This could require predicting a premature stopping of the purge process to prevent removal of too much $O_2$ that would cause a reverse overshoot. In the preferred embodiment, the purging process halts when the remaining volume is just enough to offset the longer time gas continued injections and bring the $O_2$ concentration to setpoint as $CO_2$ achieves setpoint 34, 36, 38, 56, 58, 60. This adds calculation overhead to the beginning of the rapid recovery process 28 and slows the $O_2$ reduction in concentration; however, in the two gas system when in purge mode there is no way to source $O_2$ and thus is a necessary restriction.

In different circumstances it may be preferable to select an appropriate algorithm based on each algorithm's characteristics and benefits. For instance, if a user does not require a no overshoot condition, then Algorithm 1 may be used. If a user does require a no overshoot condition but does not desire all gases to achieve setpoint relatively rapidly, then Algorithm 2 may be used. However, in some cases with respect to Algorithm 2, the lesser time gases will recover slower depending on flow rates. If a user does require a no overshoot condition and relatively rapid achievement of setpoint by all gasses, then Algorithm 3 may be used. All Algorithms 1–3 provide reduced bandwidth (i.e., they provide that constant checking of actual to setpoint is not required during recovery) and all Algorithms 1–3 can remove sensor response time error.

FIGS. 4–19 illustrate Algorithm 3 data results, as defined later herein. The inputs to the model were determined from the embedded algorithm; i.e., the full on time for $O_2/N_2$ and $CO_2$, as well as the PWM (Pulse-Width-Modulation) during the time interval in which the lesser time gas full on time has expired but the longer time gas is still actively injecting at 100% PWM were determined from simulating the embedded algorithm. Notice that depletion mode (FIGS. 4–11) corresponds to injecting $N_2$ to deplete $O_2$ and enhancement mode injects $O_2$ to raise it above normal levels. All simulations began with normal (ambient) conditions defined as 20.9% for $O_2$ and 0.3% for $CO_2$. The PWM period was defined as one second. It should also be noted that Algorithms 1 and 2 were studied in enhancement mode. Algorithm 3 provides an alternative, refined algorithm, to be utilized in a preferred example of the incubator system for control of $CO_2$ and $O_2$ levels.

FIG. 20 illustrates the basic hardware for a preferred embodiment of this invention that includes an embedded microcontroller 66, solenoid valves and orifices 64, a power board 68, and an enclosure or cabinet 70 (not airtight). Of course, pressurized gas sources 62 are also required with regulators (not shown) to set the pressure. The preferred embodiment uses $O_2/N_2$ and $CO_2$, where $O_2$ is used in $O_2$ enhancement mode and $N_2$ is supplied for depletion of $O_2$. The fixed pressure solenoid valves and orifices 64 allow the flow rate for the given gas to be determined. The algorithms reside in the embedded firmware of the microcontroller 66, which controls the solenoid valves 64.

The above description and drawings are only illustrative of preferred embodiments which achieve the objects, features, and advantages of the present invention, and it is not intended that the present invention be limited thereto. Any modification of the present invention which comes within the spirit and scope of the following claims is considered to be part of the present invention.

What is claimed is:

1. A method of controlling rapid gas recovery in an incubator system comprising:
   determining gas concentrations in the incubator to initiate rapid gas recovery;
   determining start and target volumes for each gas;
   predicting a total volume required for each gas; and
   adjusting a time required for gas recovery.

2. The method of claim 1, wherein the step of predicting the total volume required for the gas further comprises the steps of: iteratively adding injected gas and subtracting loss due to same gas injection and other gas injection based on volumetric proportions.

3. The method of claim 1, wherein a microcontroller determines gas concentrations.

4. The method of claim 1, wherein the gas is from a group including oxygen, nitrogen, and carbon dioxide.

* * * * *

UNITED STATES PATENT AND TRADEMARK OFFICE
CERTIFICATE OF CORRECTION

PATENT NO. : 7,152,455 B2 Page 1 of 1
APPLICATION NO. : 10/288462
DATED : December 26, 2006
INVENTOR(S) : Richard H. Bair, III et al.

It is certified that error appears in the above-identified patent and that said Letters Patent is hereby corrected as shown below:

On The Title Page
<u>Item (75), Inventors</u>
Please replace "Byran M. Elwood" with --Bryan M. Elwood--.

Signed and Sealed this

Twenty-ninth Day of May, 2007

JON W. DUDAS
*Director of the United States Patent and Trademark Office*